US008685731B2

(12) United States Patent
Zijlstra et al.

(10) Patent No.: US 8,685,731 B2
(45) Date of Patent: *Apr. 1, 2014

(54) PROCESS FOR THE CULTURING OF CELLS

(71) Applicant: DSM IP Assets B.V., TE Heerlen (NL)

(72) Inventors: Gerben Meile Zijlstra, Groningen (NL);
Robert Patrick Hoff, Groningen (NL);
Jacob Schilder, Kropswolde (NL)

(73) Assignee: DSM IP Assets B.V., Te Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/707,115

(22) Filed: Dec. 6, 2012

(65) Prior Publication Data

US 2013/0095527 A1 Apr. 18, 2013

Related U.S. Application Data

(63) Continuation of application No. 13/397,323, filed on Feb. 15, 2012, now Pat. No. 8,440,458, which is a continuation of application No. 12/307,995, filed as application No. PCT/EP2007/005915 on Jul. 4, 2007, now Pat. No. 8,119,368, application No. 13/707,115, which is a continuation of application No. 13/372,069, filed on Feb. 13, 2012, now Pat. No. 8,222,001.

(30) Foreign Application Priority Data

Jul. 14, 2006 (EP) ..................................... 06014671
Feb. 6, 2007 (EP) ..................................... 07002571

(51) Int. Cl.
C12N 5/02 (2006.01)

(52) U.S. Cl.
USPC ....................... 435/393; 435/297.1; 435/308.1

(58) Field of Classification Search
None
See application file for complete search history.

(56) References Cited

U.S. PATENT DOCUMENTS

| 5,019,512 | A | 5/1991 | Varecka et al. | |
|---|---|---|---|---|
| 5,053,334 | A | 10/1991 | Arathoon et al. | |
| 5,286,646 | A | 2/1994 | Kearns et al. | |
| 5,595,909 | A | 1/1997 | Hu et al. | |
| 5,871,999 | A | 2/1999 | Boraston | |
| 5,994,728 | A | 11/1999 | Uda et al. | |
| 6,022,742 | A | 2/2000 | Kopf | |
| 6,168,941 | B1 | 1/2001 | Liu et al. | |
| 6,544,424 | B1 | 4/2003 | Shevitz et al. | |
| 6,855,544 | B1 * | 2/2005 | Hateboer et al. | 435/325 |
| 6,994,128 | B2 | 2/2006 | Gleichauf et al. | |
| 2003/0054544 | A1 | 3/2003 | Gruenberg et al. | |
| 2003/0134388 | A1 | 7/2003 | Sasaki et al. | |
| 2006/0014239 | A1 | 1/2006 | Luttmann et al. | |
| 2008/0131934 | A1 | 6/2008 | Crowley et al. | |

FOREIGN PATENT DOCUMENTS

| DE | 10120835 | 11/2002 |
|---|---|---|
| EP | 0317874 | 5/1989 |
| EP | 362408 | 4/1990 |
| EP | 0248675 | 5/1992 |
| EP | 0833934 | 4/1998 |
| EP | 1354943 | 10/2003 |
| EP | 1157098 | 9/2008 |
| JP | 1085068 | 3/1989 |
| JP | 6485068 | 3/1989 |
| JP | 2001-149099 | 6/2001 |
| JP | 2002-020282 | 1/2002 |
| JP | 2002-113896 | 4/2002 |
| JP | 2003-219873 | 8/2003 |
| JP | 2005-041984 | 2/2005 |
| JP | 2008-308560 | 12/2008 |
| WO | 88/00614 | 1/1988 |
| WO | 9305145 | 3/1993 |
| WO | 96/34117 | 10/1996 |
| WO | 00/44883 | 8/2000 |
| WO | 00/63403 | 10/2000 |
| WO | 01/38362 | 5/2001 |
| WO | 03025158 | 3/2003 |
| WO | 2004-099396 A1 | 11/2004 |
| WO | 2005-095578 A1 | 10/2005 |
| WO | 2008006494 | 1/2008 |

OTHER PUBLICATIONS

Albumin-serum, MedlinePlus, downloaded Feb. 8, 2013.*
RBC count, MedlinePlus, downloaded Feb. 8, 2013.*
Nichols, et al., (2002) Propagation of adenoviral vectors: use of PER.C cells. In: Curiel D, Douglas JT, editors. Adenoviral vectors for gene therapy. San Diego: Elsevier, pp. 124-1671.
Yallop et al, (2005) PER.C6 cells for the manufacture of biopharmaceutical proteins, Modern Biopharmaceuticals: Design, Development and Optimization, 4: 779-807, Jurg Knabtein (Editor).
Freshney, R. I. (2000) Culture of animal cells (a manual of basic techniques), 4th edition, Wiley-Liss, chapters 8-9.
Baglin,et al., (1990) J Clin Pathol 43:102-105.
Third Party Observations to European Patent Application EP2041259, received at the EPO on Sep. 21, 2010.
J. Crowley et al., "Process optimization of the human cell line PER C6 for the production of biopharmaceuticals," Presented at Cell Culture Engineering IX, Mar. 7-14, 2004. Cancun, Mexico.
J. Crowley et al., "Pushing mammalian cells to the limit", in DSM Pharma Focus, Issue 14, Jun. 2004.
Furey, J. (2002) Genetic Engineering News, 22(7): pp. 62-63.
International Search and Written Opinion of the International Searching Authority for PCT/EP2007/005915, mailed Sep. 26, 2007.

(Continued)

Primary Examiner — Jim Ketter
(74) Attorney, Agent, or Firm — McDonnell Boehnen Hulbert & Berghoff LLP

(57) ABSTRACT

The invention relates to a process for the coloring of cells, preferably E1-immortalized HER cells, more preferably PER.C6 cells in a reactor in suspension in a cell culture medium, wherein the cells produce a biological substance, preferably an antibody, wherein at least one cell culture medium component is fed to the cell culture and wherein the cell culture comprising the cells, the biological substance and cell culture medium is circulated over a separation system and wherein the separation system separates the biological substance from substances having a lower molecular weight than the biological substance and wherein the biological substance is retained in or fed back into the reactor. Preferably part of the substances of lower molecular weight is continuously removed from the cell culture.

18 Claims, 5 Drawing Sheets

(56) References Cited

OTHER PUBLICATIONS

Jones et al., "Per. C6 cell line for human antibody production
Jones et al., "High level expression of the recombinant IgG in the human cell line PER.C6," Biotechnology Progress, vol. 19, (2003) pp. 163-168; XP002256988.
Xie et al., "Serum-Free Suspension Cultivation of PEr.C6 cells and recombinant adenovirus production under different PH conditions", Biotechnology and Bioengineering, (2002), vol. 80 (5), pp. 569-579, XP001155285.
http://www.crucell.com/Technology%20-%20Cell%20 Technology, printed May 3, 2011.
Lewis et al. Approaches to the release of a master cell bank of PER.C6 cells; a novel cell substrate for the manufacture of human vaccines, (2004) Dev. Biol., vol. 123: pp. 165-76. Crucell's Technology Human Glycosylation Patterns", Genetic Engineering News, (2002); vol. 22(10); pp. 50-54, XP0090187830.
Maranga et al., "Metabolism of Per. C6 cells cultivated under fed-batch conditions at low glucose and glutamine levels," Biotechnology and Bioengineering, (2006), vol. 94(1), pp. 139-150, XP002403089.
Mercille et al. (2004) Biotechnology and Bioengineering, 43(9): 833-846.
Kruse et al., (1965) The Journal of Cell Biology, 27: 273-279.
Jordan et al, (1992)"Tuning of shear sensitivity of CHO cells and its correlation with the size distribution of cell aggregates" in Animal cell technology: developments, processes and products, eds. Spier, R.E., Griffiths, J.B. and MacDonald, C. London: Butteworth-Heinemann, pp. 418-20.
Snabre et al., (1987) Biophys. J., 51: 795-807.
Moreira et al., (1992) "Aggregate suspension cultures of BHK cells" in Animal cell technology: developments, processes and products, eds. Spier, R.E., Griffiths, J.B. and MacDonald, C. London: Butteworth-Heinemann, pp. 411-413.
Maiorella et al., (1991) Biotechnol. Bioeng., 37(2): 121-126.
A/G Technology Corporation, "Operating Guide" Jan. 1999, NG Technology Corporation.
Yun-Seung Kyung, et al., (1994) Cytotechnology, 14: 183-190.
Anthony S. Lubiniecki, "Large-scale mammalian cell culture technology", CRC Press, 1990, pp. 237-240.
Gary C. Howard, et al., "Basic Methods in Antibody Production and Characterization", CRC Press, 2000, p. 91.
Michael A. Winkler, "Chemical engineering problems in biotechnology", Published by Springer, 1990, pp. 329-330.
Terence Cartwright, "Animal cells as bioreactors", Cambridge University Press, 1994, pp. 72-86.
Shepherd et al.,"Monoclonal antibodies: a practical approach", Oxford University Press, 2000, pp. 137-138.
Maureen Anne Harrison and Ian Fraser Rae, "General techniques of cell culture", Cambridge University Press, 1997, p. 128.
E.C. Beuvery et al.,"Animal Cell Technology: Developments Towards the 21st Century", Springer, 1995, p. 554.
Jerry Shevitz, et al, "Stirred tank perfusion reactors for cell propagation and monoclonal antibody production" in "Advances in Biotechnological Processes" (1989), Alan R. Liss, Inc., Chapter 11, pp. 81-106.
Norris et al.,(2002) "Growth of Cell Lines in Bioreactors," Basic Methods in Antibody Production and Characterization, CRC Press, eds. Howard, et al., p. 87-103.
Fallaux et al., (1998). Hum Gene Ther. 9(13): 1909-17.
Furey, J. "Continuous and Scalable Production from a Bioreactor" Poster presentation at the Cell Culture Engineering VII conference, Snowmass Village, Colorado, United States of America, Apr. 1-6, 2002.
Bleckwenn, N. A., Bentley, W. and Shiloach, J. "Production and Glycosylation Analysis of Model proteins from Vaccinia Virus-Mammalian Expression System", poster presentation at the 18th meeting of the European Society for Animal Cell technology (ESACT), Granada, Spain, May 11-14, 2003.
Bleckwenn N. A. et al., "Scalable Protein Production in Anchorage Dependent Mammalian Cells", poster presentation at Bioscience day conference, 2003.
Bleckwenn N. A. et al., entitled "Expression of EGPF Reporter protein with a Recombinant Vaccinia Virus—Comparison of Microcarrier and Cell Susupension Based Bioreactor Systems" poster presentation at meeting of the American Chemical Society, 2003.
Press release: "Scalable and Reliable Perfusion—Is It Really Possible?" published in the United Kingdom, Apr. 17, 2002.
Furey J. (2000) Genetic Engineering News, 20(10): 52-53.
Voisard et al., (2003) Biotechnology and Bioengineering, 82(7): 751-765.
Jorjani et al., (1999) Biotechnology and Bioengineering, 64(3):349-356.
Velez et al., (1989) Biotechnology and Bioengineering, 33(7):938-940.
Woodside et al., (1998) "mammalian cell retention devices for stirred perfusion bioreactors," Cytotechnology, Kluwer Academic Publishers, Dordrecht, NL, 28(1-3):163-175.
Banik et al., (1995) Biotechnol Prog. 11:584-588.
Belfort et al., (1994), "New Development in Membrane Bioreactors," Membrane Processes in Separation and Purification, eds. Crespo and Boddeker, pp. 127-148.
Fuchs et al., (2002) Jounral of Biotechnology, 93:243-251.
Griffiths, (2000), "Immobilized Cultures," Animal Cell Culture: A Practical Approach, Oxford University Press, eds Masters et al., p. 58-67.
Harrison et al, (1997), General Techniques of cell culture, Cambridge University Press, p. 122-138.
Horwath, (1995) "Facility Design and Validation Considerations for Continuous Cell Culture Processes," Animal Cell Technology: Developments Towards the 21st Century, Springer, eds. Reuvery, et al., p. 553-559.
Portner et al., (1995) "Evaluation of Precess Strategies for efficient cultivation of hybridoma cells based on mathematical models," Animal Cell Technology: Developments Towards the 21st Century, Springer, eds. Reuvery, et al., p. 829-831.
Risenberg et al., (1999) Appl Microbiol Biotechnol, 51:422-430.
Chu et al., (2001) Curr, Opinion Biotechn., 15(12):180-187.
Byrd et al., (1982) Nature 298: 69-75.
Byrd et al.,(1988) Oncogene 2:477-484.
Gallimore et al., P.J. (1986) Anticancer Res. 6: 499-508.
Chisti, Y, Strategies in downstream processing, in: Bioseparation and Bioprocessing: A Handbook (Subramanian, G., editor), Wiley-VCH, New York, pp. 3-30, (1998).
John R. W. Masters, Animal Cell Culture: A Practical Approach, Oxford University Press, 2000 ("Masters (2000)"); p. 59.
João C. Crespo, Karl W. Boddeker, North Atlantic Treaty Organization. Scientific Affairs Division, "Membrane processes in separation and purification", Springer, 1994 ("Crespo and Boddeker (1994)"); pp. 135-137.
Konstantinov, K.B. et al. "Control of Long-Term Perfusion Chinese Hanster Ovary Cell Culture by Glucose Auxostat" Biotechnol. Prog. vol. 12, pp. 100-109, 1996.

\* cited by examiner

PROCESS FOR THE CULTURING OF CELLS

The invention relates to a process for the culturing of cells in a reactor in suspension in a cell culture medium.

Such a process is for example known from WO04/099396. Herein it is described how the cell density of the cell culture and the yield of the desired biological material can be improved by optimizing the growth conditions in a fed-batch process.

Furthermore, WO05/095578 discloses a process for the culturing of cells by continuous perfusion culturing of a cell culture comprising cell culture medium and cells, wherein cell culture medium is added to the cell culture, the cell culture is circulated over a filter module comprising hollow fibers resulting in an outflow of liquid having a lower cell density than the cell culture, and the flow within the fitter module is an alternating tangential flow, wherein the cells produce a biological substance. In the examples of WO05/095578 it is shown that 0.9 g/L/day product is produced, corresponding to a product concentration in the outflow of approximately 0.3 g/L.

The larger the volume of liquid containing the biological substance, the more laborious becomes the purification of the biological substance. The concentration of biological substance obtained is not that high in the processes as disclosed in WO04/099396 and WO05/095578. Therefore, downstream processing of this biological substance is cumbersome, because the biological substance needs to be concentrated before further purification steps are applied or large volumes of less concentrated biological substance need to be purified. Furthermore, the culturing of cells at lower cell densities results in lower volumetric productivity and therefore requires larger and/or more culturing vessels and thus higher investments in equipment for a given production level.

Therefore, it is the object of the invention to provide a process wherein the product is obtained from the cell culture in higher concentrations.

A further object of the present invention is to enable culturing of the cells and production of the biological material during an extended period.

These objects are achieved by a process for the culturing of cells in a reactor in suspension in a cell culture medium, wherein the cells produce a biological substance, wherein at least one cell culture medium component is fed to the cell culture and wherein the cell culture comprising the biological substance and cell culture is circulated over a separation system and wherein the separation system separates the biological substance from substances having a lower molecular weight than the biological substance and wherein the biological substance is retained in or fed back into the reactor.

For example, the inventor relates to a process for the culturing of cells in a reactor in a cell culture medium, wherein the cells produce a biological substance, wherein nutrients and/or cell culture medium is/are fed to the reactor and wherein the cell culture comprising the cells and the cell culture medium is circulated over a filter having a pore size or molecular weight cut off of between 5 and 500 kD.

It has been found that by using a separation system that separates the biological substance from substances having a lower molecular weight than the biological substance, the biological substance can be accumulated in the cell culture in higher concentrations.

Hence, the present invention differs form the cell culturing described in the prior art in that it allows for accumulation of the desired biological material together with the cell mass.

In a preferred embodiment of the present invention part of the substances of lower molecular weight are continuously removed from the cell culture.

An additional advantage of the process of the present invention is that higher viable cell concentration can be reached as compared to for example batch or fed-batch processes. Furthermore, the production time—the period during which the cells produce the biological substance—can be extended compared to for example batch or fed-batch processes. Also, as compared to a batch or fed-batch process, it is possible to use a smaller reactor. Use of smaller reactors is of advantage as this reduces the equipment and facility related investments.

Also, higher concentrations of the biological substance may be obtained in shorter times.

It was found that it was possible to obtain high concentrations of biological substance within the reactor without sharply decreasing the cell viability and hence without limiting the production time. The person skilled in the art would have expected that the product inhibition, i.e. inhibition of production of the biological substance by the biological substance itself or inhibition by other macromolecules produced by the cell (such as for instance host cell proteins, enzymes or cellular debris), would occur. Furthermore, it was found that the accumulation of the desired biological material does not impair the function of the separation system.

The process of the present invention provides a considerable advantage in terms of cell density, product concentration in the cell culture and extended culturing period as compared to the processes according to WO05/095578 and WO04/099396. As a result the present process results in an improved production of the desired biological material.

Cells which can be used to produce the biological substance are in principle all cells known to the person skilled in the art, which have the ability to produce a biological product. The cells may be eukaryotic, for example, filamentous fungi, for example *Aspergillus niger, Aspergillus oryzae, Trichoderma reesei, Penicillium chrysogenum*, yeasts, for example *Saccharomyces cerevisiae, Kluyvermoyces lactis, Phaffia rhodozyma*, yeast from the genus *Pichia*, for example *Pichia pastoris* or prokaryotic, for instance *Escherichia coli, Bacillus* sp. for example *B. licheniformis, B. Subtilis, B. amyloliquefaciens, B. alkalophilus, Streptomyces* sp., *Corynebacterium glutamicum, Pseudomonas* sp. Examples of eukaryotic cells are for example also described in Chu, L., Robinson, D. K., (2001) Curr. Opinion Biotechn., vol. 12, p. 180-187. Preferably, the cells that are used in the process of the present invention are animal cells, in particular mammalian cells. Examples of mammalian cells include CHO (Chinese Hamster Ovary) cells, hybridomas, BHK (Baby Hamster Kidney) cells, myeloma cells, human cells, for example HEK-293 cells, human lymphoblastoid cells, E1 immortalized HER cells, mouse cells, for example NS0 cells. More preferably, E1 Immortalized HER cells are used, most preferably PER.C6 cells.

Primary human embryonic retina (HER) cells can be isolated from fetuses (Byrd P, Brown K W, Gallimore P H. 1982. Malignant transformation of human embryo retinoblasts by cloned adenovirus 12 DNA. Nature 298:69-71, Byrd P J, Grand R J A, Gallimore P H. 1988. Differential transformation of primary human embryo retinal cells by adenovirus E1 regions and combinations of E1A+ras. Oncogene 2:477-484). Primary cells will die upon culturing for several passages. E1-immortalized HER cells for the purpose of the present invention are derived from primary HER cells by expressing DNA encoding adenoviral E1A and E1B proteins therein, to obtain immortalized cells. Such immortalized cells can be cultured for more than 100 passages. Methods to obtain E1-immortalized HER cells have for instance been described in U.S. Pat. No. 5,994,128, in Byrd P, Brown K W, Gallimore P H. 1982. Malignant transformation of human embryo retinoblasts by cloned adenovirus 12 DNA. Nature 296: 69-71, in Byrd P J. Grand R J A, Gallimore P H. 1988. Differential transformation of primary human embryo retinal cells by adenovirus E1 regions and combinations of E1A+ras. Oncogene 2: 477-484, and in Gallimore, P. H., Grand, R. J. A. and Byrd, P. J. (1986). Transformation of human embryo retinoblasts with simian virus 40, adenovirus and ras oncogenes. Anticancer Res. 6, p499-508. For instance, immortalized HER cells, including PER.C1, PER.C3, PER.C4, PER.C5, PER.C6, PER.C8 and PER.C9 cells, were generated by transfection of primary HER cells using a plasmid that contained the adenovirus serotype 5 (Ad5) E1A- and E1B-coding sequences (Ad5 nucleotides 459-3510) under the control of the human phosphoglycerate kinase ("PGK") promoter (see U.S. Pat. No. 5,994,128).

In a preferred embodiment, the cells in the process of the present invention are E1-immortalized HER cells, more preferably PER.C6 cells (see U.S. Pat. No. 5,994,128). PER.C6 cells are exemplified by cells as deposited under ECACC No. 96022940 (see, e.g., U.S. Pat. No. 5,994,128, EP 0833934 B1).

In the process of the invention, the cells may be cultured in suspension in any form, for example as immobilized cells, single cells or in cell clusters or as a combination thereof. Preferably the cells are cultured as single cells and/or as small cell clusters of not more than 100 cells, more preferably of not more than 20 cells. Cells can for example be immobilized on microcarriers such as are commercially available from for example GE Healthcare (Cytodex).

A reactor as defined herein is a system that comprises the cell culture which cell culture on its turn comprises cells and a cell culture medium. It preferably provides sterile barriers, such as air filters, to prevent other cells from contaminating the desired cells and it preferably maintains a favorable environment for the cells by providing the right culture conditions such as mixing, temperature, pH, oxygen concentration etc.

The reactor can for example be of a more permanent nature, for example the reactor can be of stainless steel or glass or can for example be of a disposable nature, for example the reactor can be a plastic flask or bag. Examples of reactors suitable for use in the present invention include, but are not limited to stirred tank vessels, airlift vessels and disposable bags that can be mixed by rocking, shaking motion or stirring. Preferably disposable (bio)reactors are used as they are favourable as they require relatively low investment costs, have great operational flexibility, short turn-around times and are easily configurable to the process. Disposable (bio)reactors are commercially available from for example Hyclone, Sartorius, Applikon or Wave.

The term 'separation system' is defined within the framework of the invention as a system capable of separating on basis of molecular weight. The separation system used in the process of the invention is capable of separating the biological substance from substances having a lower molecular weight than the biological substance. In other words, the molecular weight cut-off is chosen such that the molecular weight cut-off (MWCO) is smaller than, more preferably at least a factor 2, most preferably at least a factor 3 smaller than the molecular weight of the biological substance. Typically, but of course depending on the molecular weight of the biological substance produced in the process of the present invention, the MWCO of the separation system is preferably at least 5, more preferably at least 10, most preferably at least 30 kDa and preferably at most 500 kDa, more preferably at most 300 kDa, most preferably at most 100 kDa. For example for an IgG with a molecular weight of 150 kDa, a separation system having a MWCO of at most 50 kDa is most preferred.

Examples of separation systems include but are not limited to filters, centrifuges and aqueous two phase extraction systems.

The term 'filter' as used herein is meant to include all devices with the ability to separate particles on basis of size or molecular weight. In principle, in the process of the present invention, any filter may be used as long as the pore size or MWCO is chosen such that the biological substance is separated from substances having a lower molecular weight than the biological substance, typically this will be a pore size or MWCO of between 5 and 500 kDa. Examples of filters suitable for use in the present invention include membrane filters, ceramic filters and metal filters. The filter may be used in any shape; the filter may for example be spiral wound or tubular or may be used in the form of a sheet. Preferably, in the process of the invention, the filter used is a membrane filter, preferably a hollow fiber filter. With the term "hollow fiber" is meant a tubular membrane. The internal diameter of the tube is at least 0.1 mm, more preferably at least 0.5 mm, most preferably at least 0.75 mm and preferably the internal diameter of the tube is at most 10 mm, more preferably at most 6 mm, most preferably at most 1 mm. Filter modules comprising hollow fibers are commercially available from for example General Electric (GE, formerly Amersham).

By circulating the cell culture comprising the biological substance, cells and the cell culture medium over a separation system, the biological substance and cells are retained in the reactor and the liquid outflow therefore has a lower concentration of biological substance and a lower cell density than the cell culture. Usually in the process of the invention, the liquid outflow does not contain or hardly contains any biological substance and cells. Usually, the liquid outflow will essentially only contain components having a molecular weight lower than that of the biological substance. Essentially all cells and essentially all biological substance are therefore usually retained in the reactor.

Preferably, the pore size or MWCO of the filter is chosen such that the size of the pores or MWCO of the filter is smaller than, more preferably at least a factor 2, most preferably at least a factor 3 smaller than the diameter or molecular weight of the product, ensuring a high retention of product. Typically, but of course depending on the size or molecular weight of use product, i.e. biological substance produced in the process of the present invention, the pore size or MWCO of the filter is preferably at least 5, more preferably at least 10, most preferably at feast 30 kDa and/or the pore size or MWCO of the filter/membrane is preferably at most 500 kDa, more preferably at most 300 kDa, most preferably at most 100 kDa.

With molecular weight cut-off (MWCO) is meant the molecular weight above which at least 90% of the particles is retained by the separation system.

Circulating the cell culture over a separation system, for example a filter means that the cell culture is passed through a separation system, for example a filter resulting in a liquid outflow and a flow which contents are kept in or fed back into the reactor. The flow which contents are kept in or fed back into the reactor will usually essentially only contain components having a molecular weight of at least equal to that of the biological substance or higher and therefore said flow will comprise more biological substance than the liquid outflow.

In principle, it is not critical when the circulation of the cell culture over the separation system is started during the process of the invention. The circulation of the cell culture may for example be started directly from the start of the process or when the viable cell density of the cells has reached a certain level.

The circulation of the cell culture over a filter may be a flow substantially perpendicular with respect to the filter surface, also known as dead-end low or a flow substantially parallel to the filter surface, also known as tangential flow, for example unidirectional tangential flow (TFF) or cross-flow. A preferred example of cross-flow is alternating tangential flow (ATF) as with ATF it was found that filter clogging does not occur (quickly) even at very high cell densities. It is common general knowledge that in depth filtration, the final small pore filter needs to be protected from clogging by course pre-filters. This practice is based on the common general knowledge that filters with smaller pores or with a smaller MWCO clog more easily, thereby limiting the production time. If ATF is used, the use of a pre-filter becomes superfluous.

The flow may be directed by moving the cell culture, by moving the filter or both. The filter may for example be moved by rotation (rotating filter) or vibration (vibrating filter). Alternatively if the flow is directed by moving the cell culture only, the filter is static and the cell culture may for example be moved by way of pumps or pressure.

With "alternating tangential flow" is meant that there is one flow in the same direction as (i.e. tangential to) the filter surface(s), which flow is going back and forth, and that there is another flow in a direction substantially perpendicular to said filter surface. Alternating tangential low can be achieved according to methods known to the person skilled in the art (for example as described in U.S. Pat. No. 6,544,424).

During the coloring of the cells, at least one cell culture medium component, for example one or more nutrients and/or cell culture medium may be fed to the cells. In the process according to the invention, it is of advantage to supplement in part or preferably in whole at least one of the depleted nutrients by way of a feed of this nutrient or these nutrients to the reactor. For example, complete cell culture medium may be led to the reactor, which is of advantage as a separate feed need then not be prepared separately. The cell culture medium may for example also be fed to the cells in a more concentrated form; this is of advantage as smaller volumes are easier to handle. Also one or more nutrients may be fed to the reactor. For example carbohydrates, for instance glucose or fructose; amino acids, such as glutamine and/or peptides may advantageously be fed to the reactor.

In a preferred embodiment of the invention, cell culture conditions are chosen such that cell growth rate and/or specific productivity of the cells is not limited and more preferably such that the concentration of at least one of the components of the cell culture medium remains essentially constant. Examples of limiting cell culture conditions are nutrient limitations and formation of inhibiting metabolites, such as ammonia, carbon dioxide and lactate. For example, cell culture conditions such as the feed may be chosen such that cell growth rate is not limited for example by supplying enough nutrients as to compensate for the depletion and/or to avoid the production of inhibiting metabolites such as lactate or ammonia. For example, the aeration conditions may be chosen such that carbon dioxide formation is not limiting the cell growth rate. Growing the cell under non-limiting conditions is highly advantageous from a Good Manufacturing Practice (GMP) point of view as 1) this may give a constant cell culture environment that in many cases also gives constant and good product quality and 2) this may lead to high cell viability, in some cases to a cell viability of more then 98%. High cell viability reduces the release of cell related contaminants, such as host cell proteins, which facilitates product purification.

Furthermore, growing the cells at unlimited cell growth rate and/or unlimited specific productivity has the commercial advantage that it is possible to produce more biological substance in an even shorter time as higher cell density will be reached earlier in the process.

"Specific productivity" of the cells is the amount of a given biological substance produced per cell per time unit and is usually expressed in $pg \cdot cell^{-1} day^{-1}$.

The rate of addition of at least one cell culture medium component, for example nutrients and/or cell culture medium to the cell culture (the inflow rate or perfusion rate) influences the viability and the density of the cells. In the process of the invention, the cell culture medium component(s), such as nutrients and/or cell culture medium may be fed for example in a continuous low, semi-continuous flow, for example stepwise flow or staggered flow. Preferably, cell culture medium component(s), for example nutrients and/or cell culture medium are added in a continuous flow.

Cell culture medium component(s), such as complete cell culture medium and/or nutrients may in principle be fed to the reactor at any time during the process. Preferably, the feed is initiated before substrates, such as glutamine and glucose have reached such low levels as to cause the growth of the cells to cease or before inhibitory metabolites, for example lactate or, ammonia reach such high levels that growth would cease. From this point onward, the cell culture medium component(s), such as nutrients and/or complete cell culture medium are preferably fed to the reactor at a rate such that substrate demand is met.

In one embodiment of the invention, cell culture medium is added at a Feed Rate according to formula (1):

$$\text{Feed Rate} = \text{SFR} \times (\text{total cell culture volume}) \times (\text{viable cell density}) \quad (1)$$

wherein the feed rate is expressed in liters per day, wherein the SFR is the Specific Feed Rate, i.e. the rate in which the cell culture medium is fed to the cell culture expressed as the volume of medium added per viable cell per time unit and wherein the viable cell density is the number of viable cells per unit of volume. The number of viable cells can be determined by the person skilled in the art, for example via the trypan blue exclusion method. The specific feed rate is preferably chosen between 0.01 and 0.3 nL/cell/day, more preferably between 0.01 and 0.2 nL/cell/day.

It may be of advantage to take into account additional parameters when adjusting the feed rate, for example the amount of glucose to be fed to the culture and/or the oxygen uptake rate. For example, for PER.C6 the feed rate of the cell culture medium and/or the nutrients is preferably chosen such that glucose concentration is kept between 3 and 20 mmol/L, more preferably between 5 and 15 mmol/L. Preferably the glucose concentration is at least 3 mmol/L, more preferably at least 5 mmol/L and preferably at most 20 mmol/L, more preferably at most 15 mmol/L.

In a special embodiment of the invention cell culture (comprising cells, biological substance and cell culture medium) is removed at least once from the reactor and liquid, for example cell culture medium or a nutrient feed is added to the reactor to compensate for the cell culture removal. Cell culture removal may lead to longer process times at high cell densities in combination with high cell viabilities resulting in a higher productivity. Cell culture may be removed continuously or step-wise.

In a preferred embodiment of the invention, cell culture (comprising cells, cell culture medium and biological substance) is removed from the reactor as soon as the desired cell density, for example a cell density of at least $10 \cdot 10^6$ viable cells/ml, preferably of at least $20 \cdot 10^6$ viable cells/ml, more preferably of at least $30 \cdot 10^6$ viable cells/ml, for example a cell density of at most $200 \cdot 10^6$ viable cells/ml, is reached and liquid, for example cell culture medium or nutrient feed is added to the reactor to compensate for the cell culture removal. Preferably, cell culture is removed at such rate that the cell density remains in the desired cell density range. This embodiment of the invention is highly advantageous as compared to a conventional batch or fed-batch process as it combines the advantages of the process of the invention with high viability that can be maintained longer, making it possible to realize an even higher overall volumetric productivity. With 'volumetric productivity' is meant the amount of biological substance produced per unit reactor volume per unit time and is usually expressed in $g \cdot L^{-1} \cdot day^{-1}$. As compared to a conventional perfusion process, this embodiment of the invention is also highly advantageous as it combines the advantages of the process of the invention with a cell culture removal stream having a high concentration of biological substance. The high concentration of biological substance in the cell culture removal stream makes it commercially interesting to harvest the biological substance there from. In a conventional perfusion process wherein cell culture is removed, the cell culture removal stream does not contain enough biological substance to make it commercially worthwhile to harvest the biological substance and the cell culture removal stream is therefore usually regarded as waste. Hence, in this embodiment of the invention, in theory all biological substance produced can be harvested in a straight forward, economically feasible and simple manner.

In a particularly preferred embodiment of the invention, cell culture conditions are chosen such that the cell growth rate and/or specific productivity of the cells is not limited and more preferably such that also the concentration of at least one of the components of the cell culture medium, such as glucose or glutamine remains constant and cell culture is removed at least once from the reactor as soon as the desired cell density is reached and liquid, for example cell culture medium is added to the reactor to compensate for the cell culture removal.

Preferably, the rate of the outflow is chosen such that it is substantially equal to the rate of the addition of the at least one cell culture medium component, for example nutrients and/or cell culture medium minus the rate of the optional cell culture removal.

Cells that produce a biological substance are for instance cells capable of expressing a gene encoding the biological substance. Cells capable of expressing a gene encoding the biological substance may for example be prepared by transaction of the cells with a plasmid containing the gene encoding the biological substance and gene encoding a suitable selection marker, for example a gene encoding a neomycine resistance (Neo marker gene). Stably transfected cells may then be selected by selection pressure, for example—in the case of a Neo marker gene—by culturing the transfected cells in the presence of G418 (genericin) and immediate screening of the cells for cells exhibiting high-level expression of the biological substance. Methods for preparing clones of E1-immortalized HER cells expressing a protein, and methods for culturing such cells to produce the protein, are well known to the skilled person, and can for instance be found in U.S. Pat. No. 6,855,544.

Biological substances, which may be produced by the cells, for example by expressing a (recombinant) gene coding therefore are for example (recombinant) proteins, in particular receptors, enzymes, fusion proteins, blood proteins such as proteins from the blood coagulation cascade, multifunctional proteins such as for instance erythropoietin, virus or bacterial proteins for instance for use in vaccines; immunoglobulins such as antibodies, for example IgG or IgM, and the like; Preferably a protein, more preferably an antibody is produced by the cells. Preferably, the biological substances such as proteins or vaccines produced by the cells can be used as an active ingredient in a pharmaceutical preparation. In the context of the present invention, the terms 'product' and 'biological substance' are interchangeable.

Within the framework of the present invention, with pharmaceutical preparation is meant any preparation, which can be used as a medicine, in particular as a medicine in humans. Such a medicine may for example be used for diagnosis, or for prophylactic purpose such as for instance a vaccine, and/or for therapeutic purpose, such as for instance an enzyme or protein for which a patent is deficient, or an antibody to kill undesired cells. A pharmaceutical preparation may further contain a pharmaceutical acceptable carrier or excipient, examples of which are well known to the person skilled in the art.

The PER.C6 cell line can be used for production of biological substances, such as E1-deleted adenovirus (see e.g. U.S. Pat. No. 6,994,128; Nichols et al, 2002, Propagation of adenoviral vectors: use of PER.C6 cells. In: Curiel D, Douglas J T, editors. Adenoviral vectors for gene therapy. San Diego: Elsevier, p 129-167), other viruses (see e.g. WO 01/38362), or recombinant proteins (see e.g. U.S. Pat. No. 6,855,544; Yallop et al, 2005, PER.C6 cells for the manufacture of biopharmaceutical proteins, Modern Biopharmaceuticals: Design, Development and Optimization, 4 Volumes, 779-807, Jörg Knäblein (Editor)).

Examples of proteins that can be used as an active ingredient in pharmaceutical preparations (with the brand name between brackets) include Tenecteplase (TN Kase™), (recombinant) antihemophilic factor (ReFacto™), lymphoblastoid Interferon α-n1 (Wellferon™), (recombinant) Coagulation factor (NovoSeven™), Etanercept, (Enbrel™), Trastuzumab (Herceptin™), Infliximab (Remicade™), Palivizumab (Synagis™), Basiliximab (Simulect™), Daclizumab (Zenapaz™), Rituximab (Rituxan™), (recombinant) Coagulation factor IX (Benefix™) and Interferon β-1a (Avonex™).

Examples of vaccines that can be used as an active ingredient in pharmaceutical preparation include isolated protein antigens, examples of which include but are not limited to live, oral, tetravalent Rotavirus vaccine (RotaShield™), rabies vaccine (RanAvert™), influenza vaccines and inactivated hepatitis A vaccine (VAQTA™).

The pH, temperature, dissolved oxygen concentration and osmolarity of the cell culture medium are in principle not critical and depend on the type of cell chosen. Preferably, the pH, temperature, dissolved oxygen concentration and osmolarity are chosen such that it is optimal for the growth and productivity of the cells. The person skilled in the art knows how to find the optimal pH, temperature, dissolved oxygen concentration and osmolarity for the culture (see. e.g. WO 2004/099396). Preferably, for the process of the invention when using E1 immortalized HER cells, the pH is chosen between 6.6 and 7.6 and/or the temperature is chosen between 30 and 39° C. and/or the osmolarity is chosen between 260 and 400 mOsm/kg. To maintain optimal process conditions automaton to control the process conditions is desired. In order to optimize process conditions, for instance to obtain growth arrest for increased cellular productivity, during the culture a shift in the culture conditions can be applied. This may be established by for instance a temperature shift (such as from 37 to 32° C.), a pH shift or an osmolarity shift.

The process of the present invention can in principle be performed in any type of cell culture medium suitable for the culturing of cells. Guidelines for choosing a cell culture medium and cell culture conditions are well known and are for instance provided in Chapter 8 and 9 of Freshney, R. I. Culture of animal cells (a manual of basic techniques), 4th edition 2000, Wiley-Liss and in Doyle, A., Griffiths, J. B., Newell, D. G. Cell & Tissue culture: Laboratory Procedures 1993, John Wiley & Sons.

For example the cell culture medium may for example comprise as a cell culture medium component a carbohydrate source, salts and/or amino acids and/or vitamins and/or lipids and/or detergents and/or buffers and/or growth factors and/or hormones and/or cytokines and/or trace elements. Examples of carbohydrate sources include glucose, fructose, galactose and pyruvate. Examples of salts include magnesium salts, for example $MgCl_2.6H_2O$, $MgSO_4$ and $MgSO_4.7H_2O$ iron salts, for example $FeSO_4.7H_2O$, potassium salts, for example $KH_2PO_4$, KCl; sodium salts, for example $NaH_2PO_4$, $Na_2HPO_4$ and calcium salts, for example $CaCl_2.2H_2O$. Examples of amino acids include all known proteinogenic amino acids, for example hystidine, glutamine, threonine, serine, methionine. Examples of vitamins include: ascorbate, bisfin, choline.Cl, myoinositol, D-panthothenate, riboflavin. Examples of lipids include: fatty acids, for example linoleic acid and oleic acid; Examples of detergents include Tween® 80 and Pluronic® F68. Example of buffers include HEPES and $Na_2CO_3$. Examples of growth factors/hormones/cytokines include IGF (insulin-like growth factor), hydrocortisone and (recombinant) insulin. Examples of trace elements are known to the person skilled in the art and include Zn, Mg and Se. The cell culture medium may for example also comprise other cell culture medium components, for example soy peptone or ethanol amine.

For production of biological substances according to the invention, in particular if the biological substances are to be used as an active ingredient in pharmaceutical preparations, serum free media are preferred to media containing a serum source. The reason for this is that serum source media may be contaminated with viruses, present the risk of prionic infections, and can create a major obstacle in the downstream processing of the biopharmaceutical product (i.e. the further purification of the biological substance from the cell culture). Therefore the process of the invention is preferably performed in a cell culture medium that does not comprise serum from an animal, including human, source. Since compounds from a mammalian source also present an infection risk, preferably the cell culture medium is mammalian source free (i.e. the cell culture medium does not comprise serum or components from a mammalian source). More preferably the cell culture medium is animal source free (i.e. the cell culture medium does not comprise serum or components from an animal, including human, source). Examples of serum free media that can be used for the culturing of PER.C6 cells include commercially available media, such as for instance EX Cell™ VPRO medium (SAFC), HyC® CDM4Retino™ (HyClone), IS ProVec CD (Irvine scientific), 293-SFM II (Invitrogen).

In preferred embodiments, the biological substance produced in the process of the present invention is harvested from the flow which contents are kept in or preferably fed back into the reactor or from the cell culture that is removed from the reactor or from both. The biological substance(s) produced in the process of the present invention can be further harvested from the cell culture in so-called downstream processing, using methods dependent on the biological substance, which methods are as such well known to the skilled person. Downstream processing usually comprises several purification steps in varying combinations and order. Examples of purification steps in the downstream processing are separation steps (e.g. by affinity chromatography and/or ion exchange chromatography and/or extraction by aqueous two-phase systems and/or precipitation by for example ammonium sulphate), steps for the concentration of the biological substance (e.g. by ultrafiltration or diafiltration), steps to exchange buffers and/or steps to remove or inactivate viruses (e.g. by virus filtration, pH shift or solvent detergent treatment).

In one aspect, the invention relates to a cell culture comprising mammalian cells, preferably E1-immortalized HER cells, more preferably PER.C6 cells, having a viable cell density of at least $50 \cdot 10^6$ cells/mL, preferably at least $60 \cdot 10^6$ cells/mL, in particular at least $90 \cdot 10^6$ cells/mL and a concentration of biological substance of at least 5 g/L, more preferably at least 10 g/L, in particular at feast 11 g/L. In principle the concentration of biological substance can be as high as the solubility of the biological substance allows. The concentration of viable cells is typically not more than $200 \cdot 10^6$ cells/mL and preferably within the range of $80\text{-}150 \cdot 10^6$ cells/mL.

Viable cell density can for example be determined using the tryptan blue exclusion method for example by using a cell counter as is commercially available from for example innovatis (Cedex cell counter).

With cell culture is meant the liquid comprising cell culture medium, cells and biological substance, which liquid is the result of a process for the culturing of cells in a reactor in a cell culture medium, wherein the cells produce the biological substance.

The invention will now be elucidated by way of the following examples without however being limited thereto.

EXAMPLES

Example 1

Comparison Between a Batch Process, a Fed Batch Process and the Process According to the Invention In this example the performance of the process according to the present invention was compared to batch and fed-batch processes.

Figure 1:
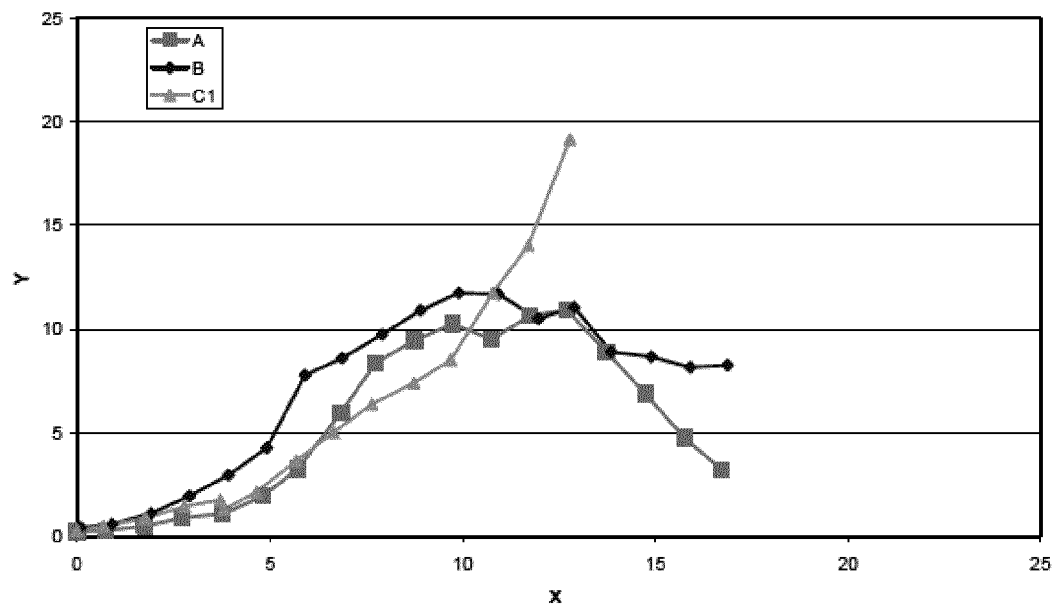
FIG. 1. shows the viable cell density Y ($10^6 \cdot ml^{-1}$) plotted versus the process time X (days) for process A (batch), B (fed-batch) and C1 (process of the invention).

FIG. 1 shows the viable cell density Y ($10^6 \cdot ml^{-1}$) plotted versus the process time X (days) for process A (batch), B (fed-batch) and C1 (process of the invention).

Figure 2:
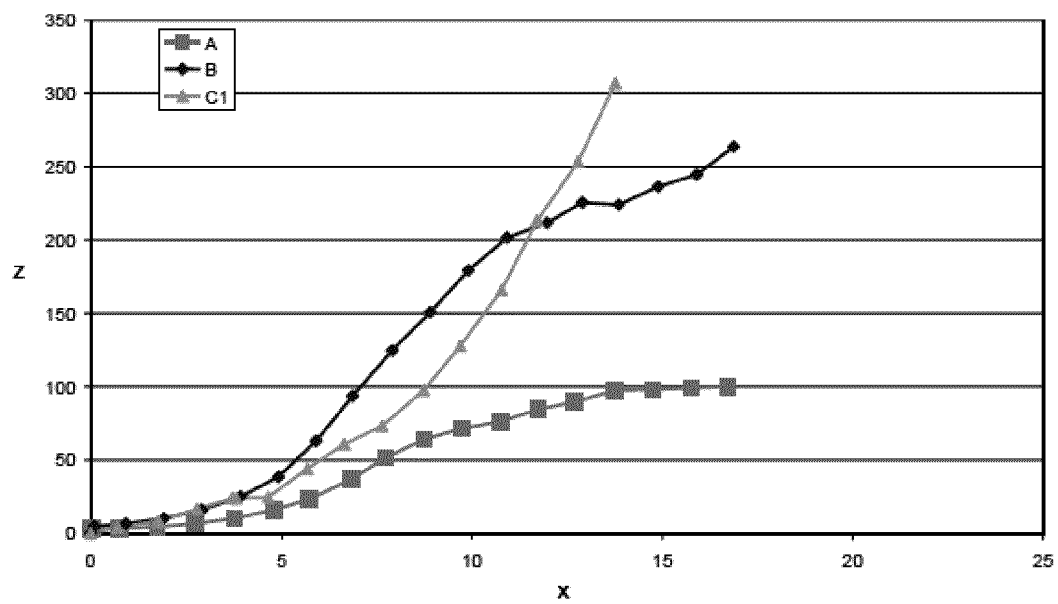
FIG. 2. shows the IgG concentration in the reactor Z (% as compared to IgG concentration in process A) versus the process time X (days) for process A (batch), B (fed-batch) and C1 (process of the invention).

FIG. 2 shows the IgG concentration in the reactor Z (% as compared to IgG concentration in process A) versus the process time X (days) for process A (batch), B (fed-batch) and C1 (process of the invention).

All fermentations were performed using a Sartorius Biostat B controller to control the temperature at 36.5° C., the pH between 7.2 and 6.8 and the DO at 50% air saturation and at 200 rpm. The same IgG producing PER.C6 cell line (see WO 2004/099396) was used in all experiments.

Batch Process A

The batch process was executed at 4 L working volume in a Sartorius B5 vessel. Cells were inoculated at 3×10e5 cells/mL in VPRO medium (SAFC) supplemented with 6 mM L-glutamin and subsequently cultured for 17 days.

Fed-Batch Process B

The fed-batch process was executed at 4 L working volume in a Sartorius B5 vessel. Cells were inoculated at 3×10e5 cells/mL in VPRO medium (SAFC) supplemented with 6 mM L-Glutamin. During the culture glucose and glutamine were added to keep toe concentration above respectively 15 mM and 1 mM. Amino acids and peptides were added from day 5 to replenish the consumed amino acids.

Process of the Invention C1

The process of the invention was performed in a 2 L Applikon vessel. A 100 kDa Molecular Weight Cut-Off (MWCO) hollow fiber membrane obtained from General Electric (GE) operated in ATF flow mode with an ATF-2 system (Refine Technology) was used to retain the cells and the IgG product. The culture was started with 3×10e5 cells/ml in VPRO medium (SAFC) supplemented with 6 mM L-Glutamin. VPRO culture medium (SAFC) supplemented with 6 mM L-Glutamin was perfused through the suspension cell culture using a Specific Flow Rate (SFR) between 0.05 and 0.2 nL/cell/day. The highest product concentration obtained was 1.4 g/L.

The process of the invention resulted in increased viable cell densities and increased product concentrations compared to mentioned cultivation modes in less time, as can be seen from FIG. 1 and FIG. 2 below.

Example 2

Comparison between a Batch Process, a Fed Batch Process and the Process According to the Invention In this example the process according to the present invention is again compared to batch and fed-batch processes; in process C2, the $CO_2$ pressure is controlled and a 50 kDa separation system was used.

Figure 3:
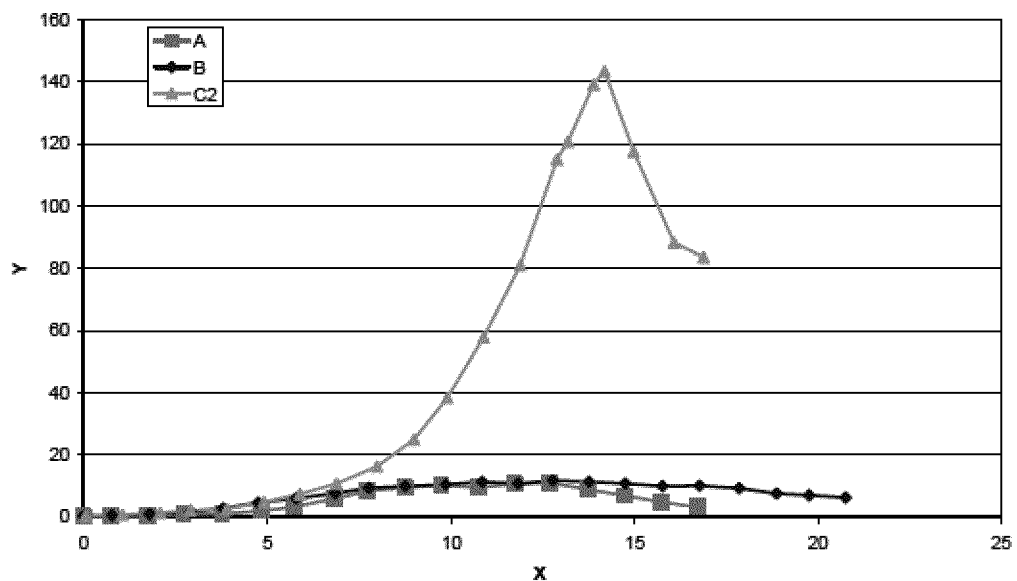
FIG. 3. shows the viable cell density Y ($10^6 \cdot ml^{-1}$) plotted versus the process time X (days) for process A (batch), B (fed-batch) C2 (process of the invention).

FIG. 3 shows the viable cell density Y ($10^6 \cdot ml^{-1}$) plotted versus the process time X (days) for process A (batch), B (fed-batch) C2 (process of the invention).

Figure 4:
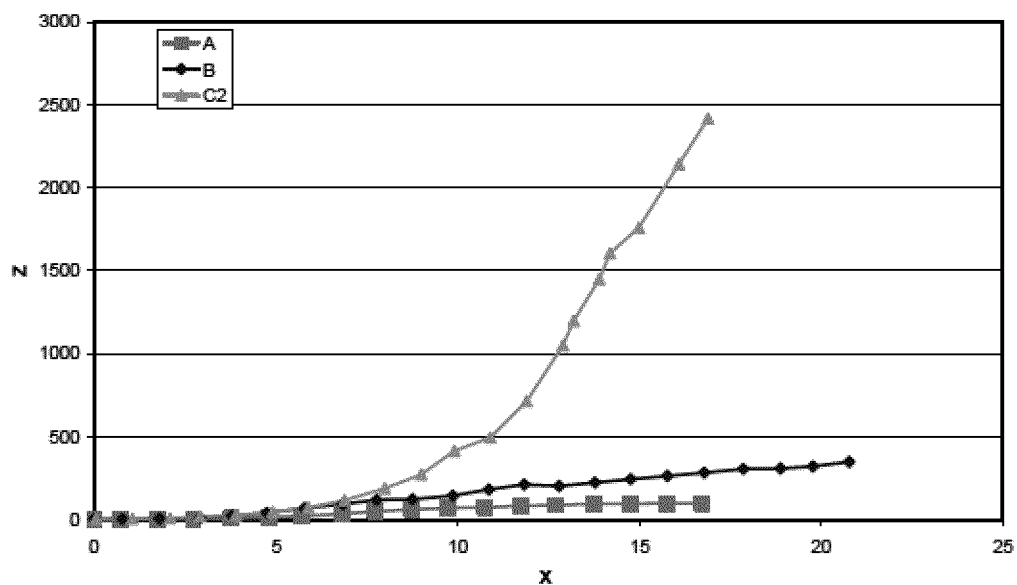
FIG. 4. shows the IgG concentration in the reactor Z (% as compared to IgG concentration in process A) versus the process time X (days) for process A (batch), B (fed-batch) and C2 (process of the invention).

FIG. 4 shows the IgG concentration in the reactor Z (% as compared to IgG concentration in process A) versus the process time X (days) for process A (batch), B (fed-batch) and C2 (process of the invention)

All fermentations were performed using a Sartorius Biostat B controller to control temperature at 36.5° C., pH between 7.2 and 6.8 and DO at 50% air saturation and at 200 rpm. The same IgG (of approximately 150 kDa) producing PER.C6 cell line (see WO 2004/099396) was used in all experiments.

Batch Process A

The batch process was executed at 4 L working volume in a Sartorius B5 vessel. Cells were inoculated at $3 \cdot 10^5$ cells·$mL^{-1}$ in VPRO medium (SAFC) supplemented with 6 mM L-glutamin and subsequently cultured for 17 days.

Fed-Batch Process B

The fed-Batch process was executed at 4 L working volume in a Sartorius B5 vessel. Cells were inoculated at $3 \cdot 10^5$ cells·$mL^{-1}$ in VPRO medium (SAFC) supplemented with 6 mM L-Glutamin. During the culture glucose and glutamine were added to keep the concentration above respectively 15 mM and 1 mM. Amino Acids and peptides were added from day 5 to replenish the consumed amino acids.

Process of the Invention C2

The process of the invention was performed in a 2 L Applikon vessel. A 50 kDa Molecular Weight Cut-Off (MWCO) hollow fiber membrane (GE) operated in ATF flow mode with an ATF-2 system (Refine Technology) was used to retain the cells and the IgG product. The culture was started with 3×10e5 cells/mL in VPRO medium (SAFC) supplemented with 6 mM L-Glutamin. VPRO culture medium (SAFC) supplemented with 6 mM L-Glutamin is perfused through the suspension cell culture using an SPR between 0.05 and 0.2 $nL \cdot cell^{-1} \cdot day^{-1}$. The $CO_2$ pressure was controlled below 15%.

Result

As can be seen from FIG. 3 and from FIG. 4, the process according to the invention results in significantly increased viable cell densities and increased product concentrations (2415%×Batch yield; 690%×Fed-Batch yield) in equal or less time (100% Batch time; 81% Fed-Batch time).

The overall productivity increase in $g \cdot L^{-1} \cdot day^{-1}$ of the process of the invention is 23.9 times the Batch productivity in $g \cdot L^{-1} \cdot day^{-1}$) and 8.5 times the Fed-batch productivity in $g \cdot L^{-1} \cdot day^{-1}$. In the process of the invention C2, 11.1 g product/L was produced. Clogging of the retention device did not occur during 17 days, even with very high cell density.

Example 3

Comparison between a Batch Process, a Fed Batch Process and the Process According to the Invention In this example the performance of the process according to the present invention with cell culture removal and again compared to batch and fed-batch processes; in process C3 cell culture has been removed.

Figure 5:
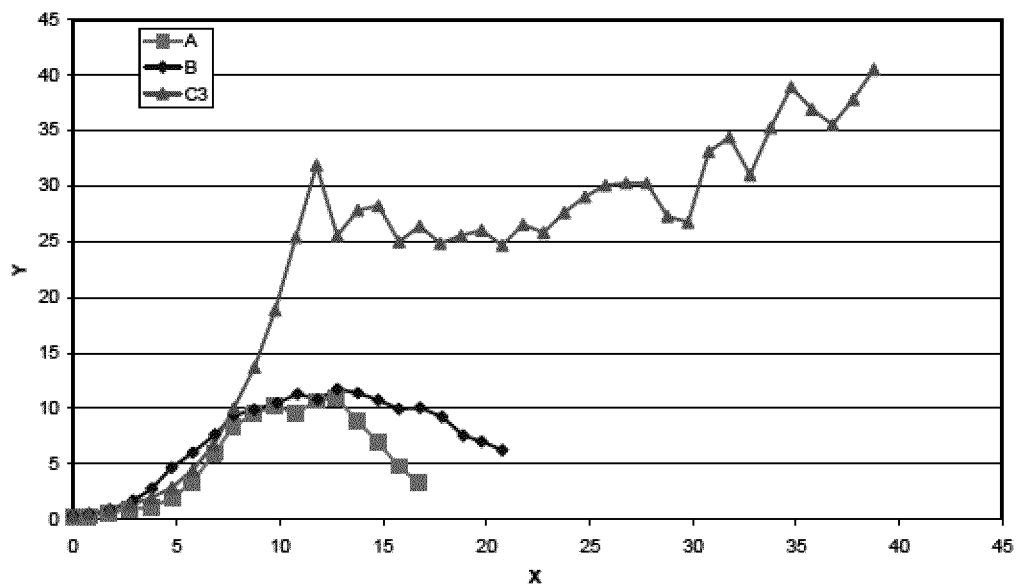
FIG. 5. shows the viable cell density Y ($10^6 \cdot ml^{-1}$) plotted versos the process time X (days) for process A (batch), B (fed-batch) C3 (process of the invention).

FIG. 5 shows the viable cell density Y ($10^6 \cdot ml^{-1}$) plotted versus the process time X (days) for process A (batch), B (fed-batch) C3 (process of the invention).

Figure 6:
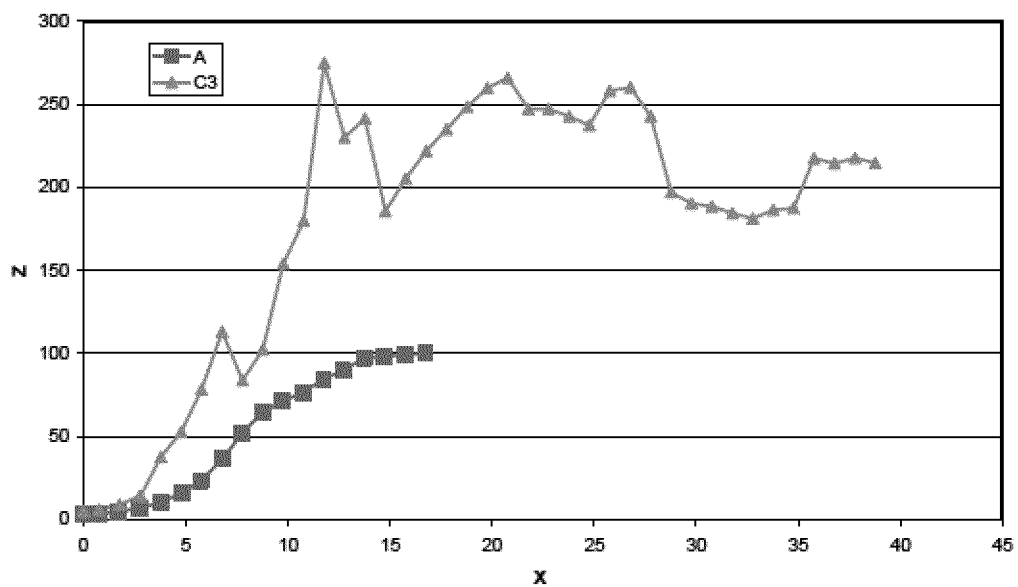
FIG. 6. shows the IgG concentration in the reactor Z (% as compared to IgG concentration in process A3) versus the process time X (days) for process A, and C3.

FIG. 6 shows the IgG concentration in the reactor Z (% as compared to IgG concentration in process A3) versus the process time X (days) for process A, and C3.

Figure 7:
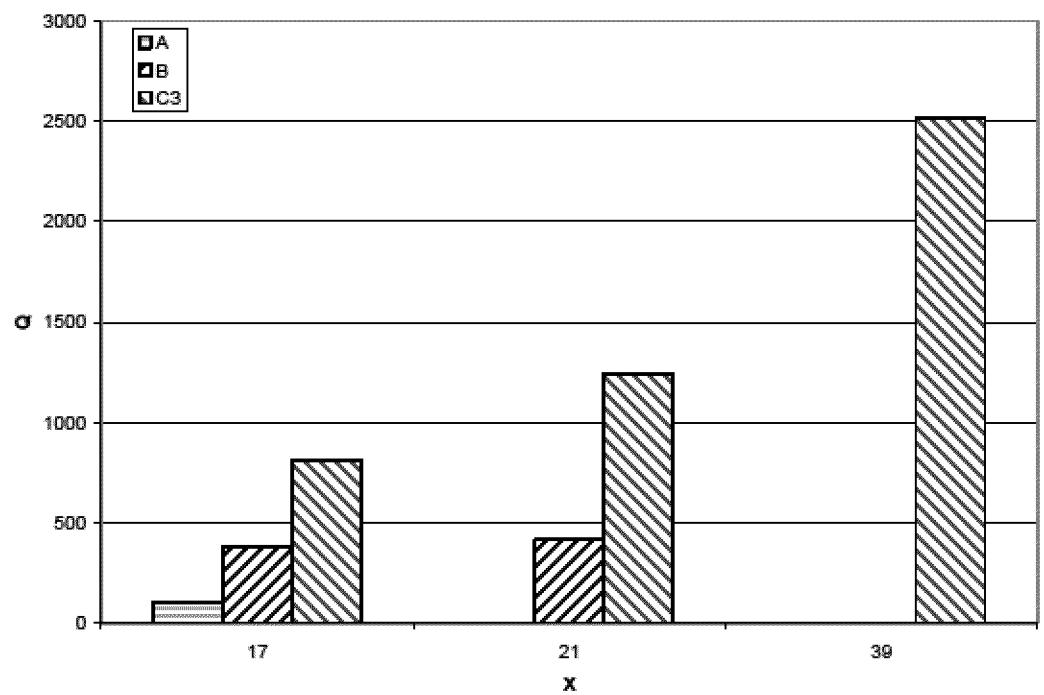
FIG. 7. shows the cumulative yield Q (% as compared to yield in process A, per L reactor volume) plotted versus the process time X (days) for process A, B and C3.

FIG. 7 shows the cumulative yield Q (% as compared to yield in process A, per L reactor volume) plotted versus the process time X (days) for process A, B and C3.

All fermentations were performed using a Sartorius Biostat B controller to control temperature at 36.5° C., pH between 7.2 and 6.8 and DO at 50% air saturation and at 200 rpm. The same IgG (of approximately 150 kDa) producing PER.C6 cell fine (see WO 2004/099396) was used in all experiments.

Batch Process A

The batch process was executed at 4 L working volume in a Sartorius B5 vessel. Cells were inoculated at $3 \cdot 10^5$ cells·mL$^{-1}$ in VPRO medium (SAFC) supplemented with 6 mM L-glutamin and subsequently cultured for 17 days.

Fed-Batch Process B

The fed-Batch process was executed at 4 L working volume in a Sartorius B5 vessel. Cells were inoculated at $3 \cdot 10^5$ cells·mL$^{-1}$ in VPRG medium (SAFC) supplemented with 6 mM L-Glutamin. During the culture glucose and glutamine were added to keep the concentration above respectively 15 mM and 1 mM. Amino Acids and peptides were added from day 5 to replenish the consumed amino acids.

Process of the Invention C3

The process of the invention was performed in a 2 L Applikon vessel. A 100 kDa Molecular Weight Cut-Off (MWCO) hollow fiber membrane (GE) operated in ATF flow mode with an ATF-2 system (Refine Technology) was used to retain the cells and the IgG product. The culture was started with 3×10e5 cells/mL in VPRO medium (SAFC) supplemented with 6 mM L-Glutamin. VPRO culture medium (SAFC) supplemented 6 mM L-Glutamin is perfused through the suspension cell culture using an SPR between 0.05 and 0.2 nL·cell$^{-1}$·day$^{-1}$. Cell culture is removed at 10% of the working volume per day above $10 \cdot 10^6$ cells·mL$^{-1}$ and at 30% of the working volume per day when the viable cell density exceeds $30 \cdot 10^6$ cells·mL$^{-1}$ and onwards.

Result

As can be seen from FIG. 5 with the process of the invention higher viable cell densities are reached fast. Furthermore, FIG. 5 also shows that the viability of the cells can be maintained longer with the process of the invention as process C3 was maintained in operation over a period of nearly 40 days, because no clogging of the retention device occurred even with high cell densities.

FIG. 6 shows that product concentrations for the process of the present invention are much higher than the product concentration in the batch process. The product flow containing the product was harvested from process C3 at approximately 200% to 250% times the final concentration in the batch process A.

FIG. 7 shows that most product is formed by the process of the present invention and that the process of the invention can be maintained longer than the batch process A or the fed-batch B. At day 17, the cumulative yield of process C3 is 8.1 times the cumulative yield of the batch process (A3) and 2.1 times the cumulative yield of the fed-batch process (B). Also, at day 17, the batch process ended. At day 21, the cumulative yield of process C3 is 3.0 times the cumulative yield of the fed-batch process B. At day 21, the fed-batch process ended. After 39 days, the overall cumulative yield of process C3 is 25 times the cumulative yield of the batch process A and 6 times the yield of the fed-batch process B.

If can be concluded from this experiment that the overall yield of a desired biological material in the process according to the present invention can be further improved by applying a bleed of the cell culture when the cell density exceeds a certain high level.

Example 4

Culturing of and Production with CHO Cells

In this example the process according to the present invention has been performed with an IgG producing CHO cell line and includes a temperature drop to decrease cell growth.

Figure 8:
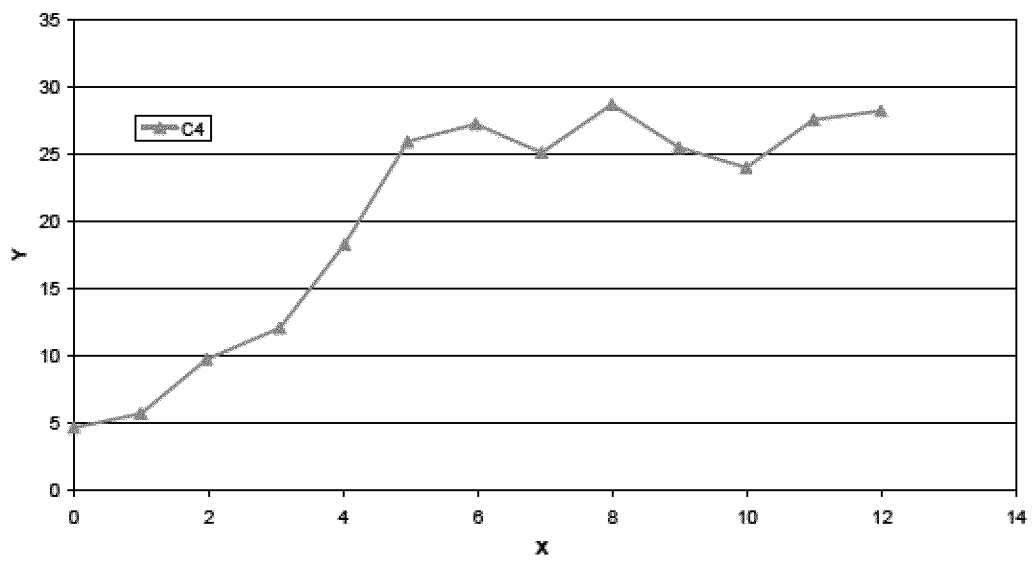
FIG. 8. shows the cell number Y ($10^6 \cdot ml^{-1}$) plotted versus the process time X (days) for C4 (process of the invention).

FIG. 8 shows the cell number Y ($10^5 \cdot ml^{-1}$) plotted versus the process time X (days) for C4 (process of the invention).

Figure 9:
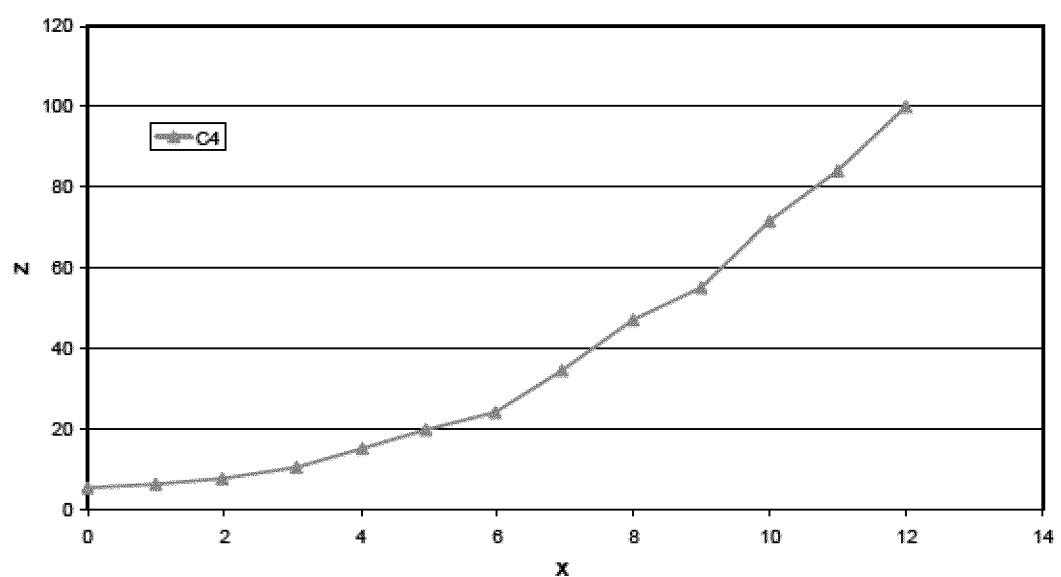
FIG. 9. shows the IgG concentration in the reactor Z (% as compared to the maximum IgG concentration reached versus the process time X (days) for process C4 (one embodiment of process of the invention)

FIG. 9 shows the IgG concentration in the reactor Z (% as compared to the maximum IgG concentration reached versus the process time X (days) for process C4 (one embodiment of process of the invention)

The fermentation was performed using a Sartorius Biostat B controller to control temperature at 36.5° C., pH between 7.1 and 6.3 and DO at 40% air saturation and at 100 rpm. The temperature was dropped to 32° C. on day 5.

Process of the Invention C4

The process of the inversion was performed in a 2 L Applikon vessel. Cell and product retention device is a 50 kD Molecular Weight Cut-Off (MWCO) hollow fiber membrane (General Electric) operated in ATF flow mode with an ATF-2 system (Refine Technology). The culture was started with $5 \cdot 10^6$ cells·mL$^{-1}$ in MTCM-49 culture medium (Hyclone). The medium was perfused through the suspension cell culture using an SPR between 0.1 and 0.4 nL·cell$^{-1}$·day$^{-1}$. The $CO_2$ pressure was controlled below 15%.

Result

The data show that the process of the invention also works when using a protein producing CHO cell line. The achieved cell density and the product concentrations are increased compared to batch culture. The data also show that in the process according to the present invention cell growth can be arrested (e.g., by a temperature drop), whereas the product accumulation in the culture system continues.

Example 5

Process of the Invention Performed with a Myeloma Cell Line

The process according to the present invention can also be applied to myeloma cell lines. To this end the fermentation is performed using a Sartorius Biostat B controller to control temperature at 36.5° C., pH between 7.2 and 6.8 and DO at 40% air saturation and at 100 rpm. The cell culturing starts with inoculating the myeloma cells at 3×10e5 cells/ml in SFM4Mab culture medium (Hyclone) in a 5 L Sartorius vessel. The cell and product retention device is a 30 kD Molecular Weight Cut-Off (MWCO) hollow fiber membrane (General Electric) operated in ATF flow mode with an ATF-4 system (Refine Technology), SFM4Mab culture medium (Hyclone) is perfused through the suspension cell culture using an SPR between 0.1 and 0.4 nL·cell-1·day-1. The $CO_2$ pressure is controlled below 15%.

Example 6

Process of the Invention Performed with an MDCK Cell Line

The process according to the present invention can also be applied to transformed MDCK cell lines in suspension. To this end the fermentation is performed using a Sartorius Biostat B controller to control temperature at 36.5° C., pH between 7.2 and 6.8 and DO at 40% air saturation and at 100 rpm. The cell culturing starts with inoculating the transformed MDCK cells at 3×10e5 cells/ml in VP-SFM culture medium (Invitrogen) in a 5 L Sartorius vessel. The cell and product retention device is a 30 kD Molecular Weight Cut-Off (MWCO) hollow fiber membrane (General Electric) operated in ATF flow mode with an ATF-4 system (Refine Technology). VP-SFM culture medium (Invitrogen) is perfused through the suspension cell culture using an SPR between 0.1 and 0.4 nL·cell-1·day-1. The $CO_2$ pressure is controlled below 15%.

The invention claimed is:

1. Process for the culturing of cells in a reactor in suspension in a cell culture medium, comprising:
   circulating a cell culture through a separation system, wherein the cell culture comprises eukaryotic cells, a biological substance produced by the cells, and a cell culture medium, wherein at least one cell culture medium component is fed to the cell culture;
   wherein the cell culture is circulated through the separation system in a tangential flow;
   wherein the separation system comprises a filter having a pore size with a molecular weight cut-off of at least 30 kDa, to separate the biological substance from substances having a lower molecular weight than the biological substance; and
   wherein the biological substance is retained in or fed back into the reactor.

2. Process according to claim 1, wherein the filter has a pore size with a molecular weight cut-off of at most 100 kDa.

3. Process according to claim 1, wherein the filter has a pore size with a molecular weight cut-off of at most 50 kDa and the biological substance is an immunoglobulin G (IgG).

4. Process according to claim 1 wherein the eukaryotic cells have a viable cell density of at least $50×10^6$ cells/ml and the concentration of the biological substance is at least 5 g/l.

5. Process according to claim 1, wherein the eukaryotic cells are mammalian cells.

6. Process according to claim 5, wherein the mammalian cells are selected from the group consisting of Chinese hamster ovary (CHO) cells, hybridomas, baby hamster kidney (BHK) cells, myeloma cells, human cells, or mouse cells.

7. Process according to claim 5, wherein the mammalian cells are CHO cells.

8. Process according to claim 1, wherein the cells have a cell viability of at least 98%.

9. Process according to claim 2 wherein the eukaryotic cells have a viable cell density of at least $50×10^6$ cells/ml and the concentration of the biological substance is at least 5 g/l.

10. Process according to claim 2, wherein the eukaryotic cells are mammalian cells.

11. Process according to claim 10, wherein the mammalian cells are selected from the group consisting of Chinese hamster ovary (CHO) cells, hybridomas, baby hamster kidney (BHK) cells, myeloma cells, human cells, or mouse cells.

12. Process according to claim 10, wherein the mammalian cells are CHO cells.

13. Process according to claim 3, wherein the cells have a cell viability of at least 98%.

14. Process according to claim 3 wherein the eukaryotic cells have a viable cell density of at least $50×10^6$ cells/ml and the concentration of the biological substance is at least 5 g/l.

15. Process according to claim 3, wherein the eukaryotic cells are mammalian cells.

16. Process according to claim 15, wherein the mammalian cells are selected from the group consisting of Chinese hamster ovary (CHO) cells, hybridomas, baby hamster kidney (BHK) cells, myeloma cells, human cells, or mouse cells.

17. Process according to claim 15, wherein the mammalian cells are CHO cells.

18. Process according to claim 3, wherein the cells have a cell viability of at least 98%.

* * * * *